United States Patent
Enghard et al.

(10) Patent No.: US 12,292,436 B2
(45) Date of Patent: May 6, 2025

(54) METHOD FOR PRESERVING URINARY CELLS

(71) Applicant: CHARITÉ-UNIVERSITÄTSMEDIZIN BERLIN, Berlin (DE)

(72) Inventors: Philipp Enghard, Berlin (DE); Paul Freund, Berlin (DE); Diana Metzke, Berlin (DE); Christopher Skopnik, Berlin (DE)

(73) Assignee: CHARITÉ-UNIVERSITÄTSMEDIZIN BERLIN, Berlin (DE)

( * ) Notice: Subject to any disclaimer, the term of this patent is extended or adjusted under 35 U.S.C. 154(b) by 918 days.

(21) Appl. No.: 17/298,618

(22) PCT Filed: Dec. 19, 2019

(86) PCT No.: PCT/EP2019/086433
§ 371 (c)(1),
(2) Date: May 31, 2021

(87) PCT Pub. No.: WO2020/127815
PCT Pub. Date: Jun. 25, 2020

(65) Prior Publication Data
US 2022/0003748 A1    Jan. 6, 2022

(30) Foreign Application Priority Data

Dec. 19, 2018 (EP) .................................... 18214037

(51) Int. Cl.
*G01N 33/50* (2006.01)
*G01N 1/28* (2006.01)
*G01N 15/1404* (2024.01)

(52) U.S. Cl.
CPC .......... *G01N 33/5005* (2013.01); *G01N 1/28* (2013.01); *G01N 15/1404* (2013.01); *G01N 2800/34* (2013.01)

(58) Field of Classification Search
CPC .. G01N 33/5005; G01N 1/28; G01N 15/1404; G01N 2800/34; G01N 33/5044; G01N 33/505; G01N 33/50
See application file for complete search history.

(56) References Cited

U.S. PATENT DOCUMENTS 5,459,073 A    10/1995  Ryan
6,794,152 B2 *  9/2004  Ryan .................. G01N 33/5094
                                                      436/15

FOREIGN PATENT DOCUMENTS

CN    108642042    10/2018
EP    3064597      9/2016
(Continued)

OTHER PUBLICATIONS

"Common buffers, media, and stock solutions." Current Protocols in Human Genetics, John Wiley & Sons. 26: Appendix 2D, pp. A.2D.1-A.2D.13 . (published online: May 1, 2001). https://doi.org/10.1002/0471142905.hga02ds26 (Year: 2001).*
(Continued)

*Primary Examiner* — Aaron J Kosar
(74) *Attorney, Agent, or Firm* — JMB Davis Ben-David

(57) ABSTRACT

The present invention relates to a method for preserving urinary cells, the method comprising the step of contacting a urine sample obtained from a patient with a buffer substance suitable to create and/or maintain a pH value in the range of 6 to 8, particularly approx. 7, within said urine sample, and a formaldehyde releasing compound.

11 Claims, 11 Drawing Sheets

(56) References Cited

FOREIGN PATENT DOCUMENTS

| | | | |
|---|---|---|---|
| WO | 2014029791 | 2/2014 | |
| WO | WO-2014029791 A1 * | 2/2014 | ......... C12N 15/1003 |

OTHER PUBLICATIONS

C Lv et al "investigation on formaldehyde release from preservatives in cosmetics" Int J Cosmet Sci. Oct. 2015; 37(5):474-8.Epub Mar. 9, 2015.

* cited by examiner

METHOD FOR PRESERVING URINARY CELLS

CROSS-REFERENCE TO RELATED APPLICATIONS

This is the U.S. National Stage of International Patent Application No. PCT/EP2019/086433 filed on Dec. 19, 2019, which in turn claims the benefit of European Patent Application No. 18214037.6 filed on Dec. 19, 2018.

BACKGROUND OF THE INVENTION

Flow cytometry (fluorescence-activated cell sorting, FACS) is a powerful technology which allows simultaneous quantification of several antigens on single cell level. This is done by labelling the cell-bound antigens with fluorochrome-coupled antibodies. This procedure is referred to as staining. Urine in healthy people is normally almost free of leukocytes and other cells. In various kidney diseases, however, increased amounts of kidney and immune cells are found in the urine. Flow cytometric analysis of human urinary cells is a promising diagnostic tool for renal diseases. For example, the amount of T cells in the urine indicates the extent of inflammation in renal tissue whereas renal tubule epithelial cells (TECs) are global stress and renal damage markers. It has been demonstrated that the number of urinary T cells in patients with Systemic Lupus Erythematosus (SLE) correlates with renal involvement of the disease, i.e. Lupus Nephritis (Class III & IV)—a common and severe complication of SLE. This also applies for refractory cases. In further renal diseases such as Acute Kidney Injury (AKI), Renal Transplant Rejection and ANCA Vasculitis, flow cytometric analysis of urinary cells as a biomarker has shown encouraging results. It is believed that all renal and urological diseases may potentially be monitored using flow cytometry of urinary cells. Thus, using this method in clinical practice for diagnostics as well as monitoring of therapy could be a useful addition to the current routine tests for renal diseases.

As today, fresh urine samples of patients are needed to allow flow cytometric analysis of urinary cells, i.e. time between voiding of a urine sample and a first centrifugation step should not exceed six hours. Ideally, time is kept as short as possible. This requirement can be fulfilled in large hospitals with appropriate infrastructure, i.e. laboratories for sample preparation. However, it makes the analysis expensive and smaller clinics as well as medical practices are excluded from sample submission. In order to solve this logistic limitation, the inventors have developed a method for conserving urinary cells directly within the urine.

Based on the above, it is the objective of the present invention to provide simple and reliable means and method for preserving or conserving urinary cells.

SUMMARY OF THE INVENTION

The present invention aims to provide means and methods to preserve cells in a urine sample in such a way that they are stable for more than 4 to 6 hours prior to analysis but are also suitable for an analysis, e.g. by antibody based methods such as FACS. The sample treatment according to the invention would allow the storage and/or transport of a urine sample prior to the analysis. The preservation does not change the cells in such a way that no meaningful staining for flow cytometric analysis is possible.

This objective is attained by using a buffer substance to adjust and maintain the pH between pH 6 and pH 8 and by adding a formaldehyde releasing compound to the urine sample. Cells that are present in the urine may be detected or analyzed in a subsequent analysis step. A suitable method for such detection or analysis is FACS. By using specific antibody combinations, different cell types can be detected and quantified, which allows assignment to a healthy condition or a specific disease or subtype of a disease. Also the progression of a disease or the progress of treatment may be monitored by the means and methods described herein.

A first aspect of the invention relates to a method for analysing urinary cells. The method comprises the steps of:
  contacting a urine sample obtained from a patient with
    a. a buffer substance suitable to create and/or maintain a pH value in the range of 6 to 8, particularly approx. pH 7, within said urine sample, and
    b. a formaldehyde releasing compound yielding a preserved urine sample,
  analysing urinary cells within said preserved urine sample.

Another aspect of the invention relates to a method for diagnosing a medical condition. The method comprises analysing urine cells within a urine sample obtained from a patient with a method according to the first aspect of the invention.

Yet another aspect of the invention relates to a container suitable for preserving urinary cells in a urine sample comprising a formaldehyde releasing compound, and a buffer substance able to maintain at a pH in the range of 6 to 8, particularly approx. 7, in a urine sample.

DETAILED DESCRIPTION OF THE INVENTION

Terms and Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

The terms "comprising," "having," "containing," and "including," and other similar forms, and grammatical equivalents thereof, as used herein, are intended to be equivalent in meaning and to be open ended in that an item or items following any one of these words is not meant to be an exhaustive listing of such item or items, or meant to be limited to only the listed item or items. For example, an article "comprising" components A, B, and C can consist of (i.e., contain only) components A, B, and C, or can contain not only components A, B, and C but also one or more other components. As such, it is intended and understood that "comprises" and similar forms thereof, and grammatical equivalents thereof, include disclosure of embodiments of "consisting essentially of" or "consisting of."

Where a range of values is provided, it is understood that each intervening value, to the tenth of the unit of the lower limit, unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

Reference to "about" a value or parameter herein includes (and describes) variations that are directed to that value or parameter per se. For example, description referring to "about X" includes description of "X."

As used herein, including in the appended claims, the singular forms "a," "or," and "the" include plural referents unless the context clearly dictates otherwise.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc.) and chemical methods.

The term "buffer substance" in the context of the present specification is used in its meaning known in the art; it particularly refers to a weak acid or base and it conjugate base or acid. A suitable buffer substance to create and/or maintain a pH value in the range of 6 to 8 is preferable characterized by at least one $pK_A$ value in the range of 6 to 8.

The term "formaldehyde releasing compound" in the context of the present specification particularly refers to a compound that releases formaldehyde, particularly slowly but not spontaneously, for example in the presence of water or a suitable aqueous buffer solution. Suitable formaldehyde releasing compounds are characterized by a formaldehyde release of up to 20 mg/L, particularly 1 mg/L to 15 mg/L, more particularly 5 mg/L to 15 mg/L, at one hour after dissolving 0.1% (w/v) of the formaldehyde releasing compound in an aqueous solution (pH 7) at 25° C. Formaldehyde releasing compounds are also commonly known as formaldehyde releasers. For the purpose of the current specification, the term "formaldehyde releasing compound" excludes formaldehyde and paraformaldehyde.

The term "urinary cells" in the context of the present specification refers to cells that are found in the urine. The term also encompasses cells that not naturally present in urine, for example cancer cells, etc. The urinary cells are mammalian cells, particularly human cells.

The objective is attained by a method according to the first, second or third aspect of the invention and a container according to the fourth aspect of the invention. Preferred embodiments are stated in the dependent claims and the following description.

A first aspect of the invention relates to a method for preserving urinary cells. The method comprises the step of:
  contacting a urine sample obtained from a patient with
   a. a buffer substance suitable to create and/or maintain a pH value in the range of 6 to 8 within the urine sample, and
   b. a formaldehyde release compound.

In certain embodiments, the urine sample is contacted simultaneously with the buffer substance and the formaldehyde releasing compound or the urine sample is first contacted with the buffer substance and then the formaldehyde releasing compound is added.

In certain embodiments, the urine sample is contacted simultaneously with the buffer substance and the formaldehyde releasing compound.

In certain embodiments, the urine sample is first contacted with the buffer substance and then the formaldehyde releasing compound is added.

In certain embodiments, the method consists of the step of contacting a urine sample obtained from a patient with a buffer substance suitable to create and/or maintain a pH value in the range of pH 6 to pH 8 within the urine sample, and a formaldehyde releasing compound.

In certain embodiments, the buffer substance is suitable to create and/or maintain a pH value in the range of 6.9 to 7.4 within the urine sample.

In certain embodiments, the said urine sample is contacted with the buffer substance and the formaldehyde releasing compound not later than 6 h, 5 h, 4 h, 3 h, 2 h, or 1 h after sampling, particularly immediately after sampling.

Preferably, the buffer substance is in such a concentration when contacted with the urine sample that within the urine sample the desired pH value, e.g. 7.2 to 7.4, forms without need of further adjustment, e.g. by additionally adding an acid or a base.

In certain embodiments, the formaldehyde releasing compound is selected from imidazolium urea (CAS No 39236-46-9), hexamethylenetetramine chloroallyl chloride (CAS No 4080-31-3), diazolidinyl urea (CAS No 78491-02-8), 1,3-bis(hydroxymethyl)-5,5-dimethylimidazolidine-2,4-dione (DMDM hydantoin, CAS No 6440-58-01), 1-(hydroxymethyl)-5,5-dimethyl-2,4-imidazolidindione (MDM hydantoin) or hexamethylenetetramine (urotropin, CAS No 100-97-0).

In certain embodiments, the formaldehyde releasing compound is not paraformaldehyde.

In certain embodiments, the buffer substance is selected from 3-(N-morpholino)propanesulfonic acid (MOPS), phosphate buffered saline (PBS), sodium hydrogencarbonate, tris(hydroxymethyl)aminomethane (TRIS) and 4-(2-hydroxyethyl)-1-piperazineethanesulfonic acid (HEPES).

In certain embodiments, the buffer substance is selected from 3-(N-morpholino)propanesulfonic acid (MOPS), phosphate buffered saline (PBS), and 4-(2-hydroxyethyl)-1-piperazineethanesulfonic acid (HEPES).

In certain embodiments, the buffer substance is provided in a buffer solution.

In certain embodiments, the concentration of the buffer substance in the buffer solution is between 0.2 mol/l and 5 mol/l.

In certain embodiments, the concentration of the buffer substance in the buffer solution is between 0.5 mol/l and 2 mol/l.

In certain embodiments, the concentration of the buffer substance in the buffer solution is 1 mol/l.

In certain embodiments, the urine sample is further contacted with a chelating compound selected from 2,2',2",2"'-(ethane-1,2-diyldinitrilo)tetraacetic acid (EDTA), ethylene glycol-bis(2-aminoethylether)-N,N,N',N'-tetraacetic acid (EGTA) and 2,2',2"-nitrilotriacetic acid (NTA).

In certain embodiments, the urine sample is further contacted with EDTA.

To prevent precipitation of formaldehyde in urine, the buffer substance may be added to the urine sample before the formaldehyde releasing compound is added.

In certain embodiments, the urine sample is contacted first with the buffer substance and then with the formaldehyde releasing compound.

To achieve a balance between sufficient preservation of the cells in the urine sample and sufficient antibody staining in the analysis step, the final concentration of the formaldehyde releasing compound in the preserved sample directly after the contacting step is between 0.5% (w/v) and 5%

(w/v). The preservation does not change the cells in such a way that no meaningful staining for flow cytometric analysis is possible.

In certain embodiments, the final concentration of the formaldehyde releasing compound is between 0.5% (w/v) and 5% (w/v).

In certain embodiments, the final concentration of the formaldehyde releasing compound is between 1% (w/v) and 3% (w/v).

In certain embodiments, the final concentration of the formaldehyde releasing compound is 2% (w/v).

To maintain a pH between pH 6 and pH 8 to prevent the precipitation of formaldehyde in urine as a gel-like mass, the final concentration of the buffer substance in the preserved sample directly after the contacting step is between 5% (w/v) and 10% (w/v).

In certain embodiments, the final concentration of the buffer substance is between 5% (w/v) and 10% (w/v).

In certain embodiments, the final concentration of the buffer substance is 7% (w/v).

In certain embodiments, the final concentration of the buffer substance is between 5% (w/v) and 10% (w/v), particularly 7% (w/v), and the final concentration of the formaldehyde releasing compound is between 0.5% (w/v) and 5% (w/v), particularly between 1% (w/v) and 3% (w/v).

The preserved sample may be stored at 4° C. up to one month prior to analysing the cells. It is also possible to freeze the preserved sample.

In certain embodiments, the preserved sample is stored prior to analysing the urinary cells.

In certain embodiments, the preserved sample is stored prior to analysing the urinary cells at a temperature ≤10° C., particularly ≤4° C.

In certain embodiments, the preserved sample is stored prior to analysing the urinary cells at a temperature between −80° C. and 10° C., particularly −80° C. and 4° C.

In certain embodiments, the preserved sample is stored prior to analysing the urinary cells at a temperature between −20° C. and 10° C., particularly −20° C. and 4° C.

A second aspect of the invention relates to a method for analysing urinary cells. The method comprises the steps of:
providing a urine sample obtained from a patient,
preserving the urine sample with a method according to the first aspect of the invention or any embodiment thereof, thereby yield a preserved urine sample, and
analysing urinary cells within the preserved urine sample.

In certain embodiments, analysing comprises a cytometric analysis of the urinary cell in the preserved urine sample, e.g. measurement of cell size, cell count cell morphology (shape and structure), cell cycle phase, DNA content, cell surface proteins, etc. In certain embodiments, the cyctometric analysis is or comprises a flow cytometric analysis, particularly fluorescence-activated cell sorting (FACS).

A third aspect of the invention relates to a method for diagnosing a medical condition. The method comprises analysing urinary cells in a urine sample obtained from a patient with a method according to the second aspect of the invention or any embodiment thereof.

In certain embodiments, the medical condition is selected from Lupus nephritis, acute Kidney Injury, rejection after kidney transplantation, ANCA vasculitis, diabetic nephropathy, IgA nephropathy, nephrolithiasis (renal stones), and bladder cancer.

In certain embodiments, the medical condition is Lupus nephritis and the presence and/or quantity of a surface marker selected from CD3, CD4, CD8, CD45RA, CD45RO, CCR7, CD14, CD36 is determined on the urinary cells within the preserved urine sample.

In certain embodiments, the medical condition is renal transplant rejection and the presence and/or quantity of a surface marker selected from CD3, CD4, CD8, CD45RA, CD45RO, CCR7, CD14, CD69 CD36, Podocalyxin, Cytokeratin, CD10, CD13, EPCAM, CD227 is determined on the urinary cells within the preserved urine sample.

In certain embodiments, the medical condition is acute kidney injury and the presence and/or quantity of a surface marker selected from CD3, CD4, CD8, CD45RA, CD45RO, CCR7, CD14, CD36, Podocalyxin, Cytokeratin, Podocin (PDCN, SRN1) nephrin (NPHN, NPHS1), Wilms Tumour Protein (WT1), CD10, CD13, EPCAM, CD227 is determined on the urinary cells within the preserved urine sample.

In certain embodiments, the medical condition is ANCA associated glomerulonephritis and the presence and/or quantity of a surface marker selected from CD3, CD4, CD8, CD45RA, CD45RO, CCR7, CD14, CD36, Podocalyxin, Cytokeratin, CD10, CD13, EPCAM, CD227 is determined on the urinary cells within the preserved urine sample.

A fourth aspect of the invention relates to a container suitable for preserving urinary cells in a urine sample. The container comprises
a formaldehyde releasing compound, and
a buffer substance able to create and/or maintain at a pH in the range of 6 to 8 in a urine sample.

In certain embodiments, the container comprises an inner volume, wherein a composition is present in said inner volume and wherein the composition comprises, particularly consists of,
a formaldehyde releasing compound selected from imidazolium urea, hexamethylenetetramine chloroallyl chloride, diazolidinyl urea, 1,3-bis(hydroxymethyl)-5,5-dimethylimidazolidine-2,4-dione, 1-(hydroxymethyl)-5,5-dimethyl-2,4-imidazolidindione or hexamethylenetetramine, and
a buffer substance able to maintain at a pH in the range of pH 6 to pH 8, particularly approx. pH 7, in a urine sample.

Particularly, the container is configured to receive and hold a fluid, particularly a urine sample.

In certain embodiments, the container is a tube and comprises a sealable opening, through which the urine sample may be transferred into the container. Alternatively, the container may be a urine cup. Preferably, the patient or medical staff can add the urine specimen or sample immediately to the container and store it directly in the fridge after inverting it several times.

In certain embodiments, the formaldehyde releasing compound and/ or the buffer substance are present in the container in solid form, e.g. in form of a powder, tablets or a granulate.

In certain embodiments, the formaldehyde releasing compound is selected from imidazolium urea, hexamethylenetetramine chloroallyl chloride, diazolidinyl urea, 1,3-bis(hydroxymethyl)-5,5-dimethylimidazolidine-2,4-dione., 1-(hydroxymethyl)-5,5-dimethyl-2,4-imidazolidindione or hexamethylenetetramine.

In certain embodiments, the formaldehyde releasing compound is not paraformaldehyde.

In certain embodiments, the buffer substance is selected from 3-(N-morpholino)propanesulfonic acid, phosphate buffered saline, sodium hydrogencarbonate, tris(hydroxymethyl)aminomethane and 4-(2-hydroxyethyl)-1-piperazineethanesulfonic acid.

In certain embodiments, the buffer substance is selected from 3-(N-morpholino)propanesulfonic acid, phosphate buffered saline, sodium hydrogencarbonate, and 4-(2-hydroxyethyl)-1-piperazineethanesulfonic acid.

In certain embodiments, the ratio of the amount of formaldehyde releaser to the amount of buffer substance is between 1:10 and 1:2, particularly between 1:5 and 2:5.

In certain embodiments, the ratio of the amount of formaldehyde releaser to the amount of buffer substance is 2:7.

The invention further encompasses the following embodiments, without being limited thereto:

Embodiment 1: A method for preserving urinary cells, the method comprising the step of:
contacting a urine sample obtained from a patient with
a. a buffer substance suitable to create and/or maintain a pH value in the range of 6 to 8, particularly approx. 7, within said urine sample, and
b. a formaldehyde releasing compound.

Embodiment 2: The method according to embodiment 1, wherein said urine sample is contacted with said buffer substance and said formaldehyde releasing compound not later than 6 h, 5 h, 4 h, 3 h, 2 h or 1 h after sampling, particularly immediately after sampling.

Embodiment 3: The method according to embodiment 1 or 2, wherein said formaldehyde releasing compound is selected from imidazolium urea, hexamethylenetetramine chloroallyl chloride, diazolidinyl urea, 1,3-bis(hydroxymethyl)-5,5-dimethylimidazolidine-2,4-dione., 1-(hydroxymethyl)-5,5-dimethyl-2,4-imidazolidindione or hexamethylenetetramine.

Embodiment 4: The method according to any one of the preceding embodiments, wherein said suitable buffer substance is selected from 3-(N-morpholino)propanesulfonic acid, phosphate buffered saline sodium hydrogencarbonate, tris(hydroxymethyl)aminomethane and 4-(2-hydroxyethyl)-1-piperazineethanesulfonic acid.

Embodiment 5: A method for analysing urinary cells, comprising
providing a urine sample obtained from a patient,
preserving said urine sample with a method according to any one of embodiments 1 to 4, thereby yield a preserved urine sample, and
analysing urinary cells within said preserved urine sample.

Embodiment 6: The method according to embodiment 5 wherein said analysing comprises a cytometric analysis of said urinary cells with said preserved urine sample.

Embodiment 7: The method according to embodiment 6, wherein said cytometric analysis comprises a flowcytometric analysis, particularly FACS.

Embodiment 8: A method for diagnosing a medical condition, the method comprising analysing urine cells within a urine sample obtained from a patient with a method according to any one of embodiments 5 to 7.

Embodiment 9: The method according to embodiment 8, wherein said medical condition is selected from Lupus nephritis, acute kidney injury, rejection after kidney transplantation, ANCA vasculitis, diabetic nephropathy, IgA nephropathy, nephrolithiasis, and bladder cancer.

Embodiment 10: A container suitable for preserving urinary cells in a urine sample comprising
a formaldehyde releasing compound, and
a buffer substance able to maintain at a pH in the range of 6 to 8, particularly approx. 7, in a urine sample.

Embodiment 11: The container according to embodiment 10, wherein said formaldehyde releasing compound is selected from imidazolium urea, hexamethylenetetramine chloroallyl chloride, diazolidinyl urea, 1,3-bis(hydroxymethyl)-5,5-dimethylimidazolidine-2,4-dione., 1-(hydroxymethyl)-5,5-dimethyl-2,4-imidazolidindione or hexamethylenetetramine.

Embodiment 12: The container according to embodiment 10 or 11, wherein said buffer substance is selected from 3-(N-morpholino)propanesulfonic acid, phosphate buffered saline, sodium hydrogencarbonate, tris(hydroxymethyl)aminomethane and 4-(2-hydroxyethyl)-1-piperazineethanesulfonic acid.

The invention is further illustrated by the following examples and figures, from which further embodiments and advantages can be drawn. These examples are meant to illustrate the invention but not to limit its scope.

EXAMPLES

Example 1: Preserving and Analyzing Urine Cells

Fixation of cells and tissues with agents such as formaldehyde is considered routine practise in laboratories. The basis of this fixation is cross-linking of proteins at certain amino acids.

Figure 1:
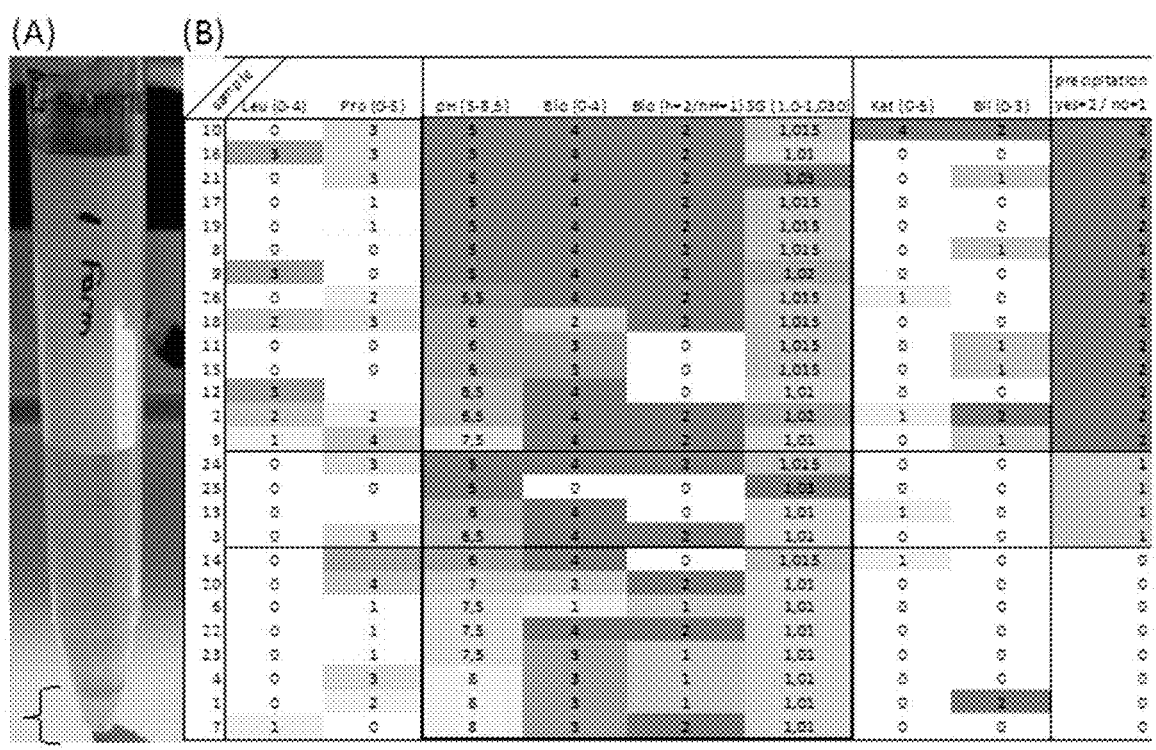
FIG. 1 shows the relation between pH values and precipitate formation in urine. Especially specimen with low pH values tend to form precipitation. (A) Example of precipitation of patient's urine with added formaldehyde after 22 hours (+/−2 hours). (B) Dipstick results and relation to precipitation of urine with added formaldehyde after 22 hours (+/−2 hours)

When adding formaldehyde directly to the urine of patients the inventors observed precipitation of a gel-like mass in a significant number of samples after approximately 22 hours, thus making it impossible to analyse the samples on the next day. Dipstick results of patient's urine specimens suggest that especially samples with low pH tend to form precipitation (FIG. 1).

Following the assumption that low pH triggers precipitation, the inventors added a standard cell culture buffer (MOPS) to urine samples together with formaldehyde. By stabilizing the pH closer to neutral the inventors were able to avoid precipitation. Further neutralizing strategies were tested as well, for example dilution with distilled water or other buffers (PBS), but resulted either in more precipitation or worse quality in FACS analysis when compared to MOPS buffer in corresponding conditions.

Figure 2:
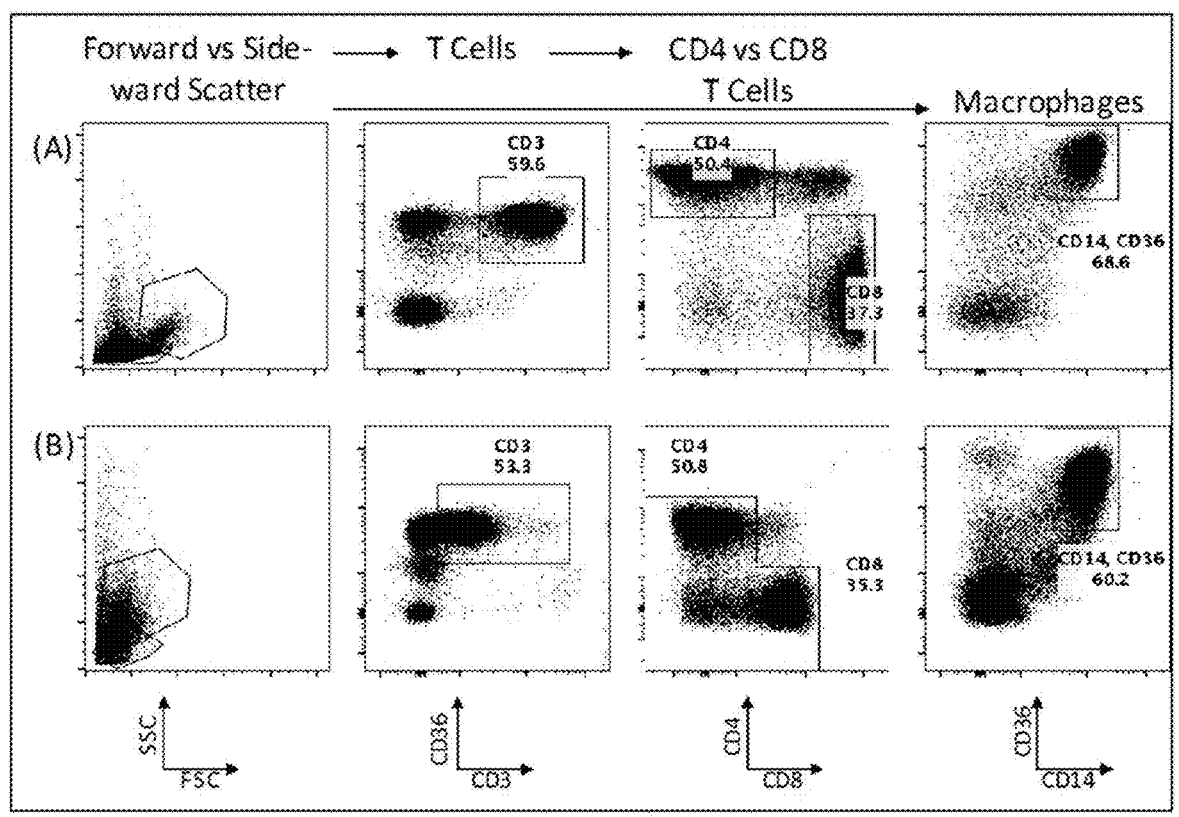
FIG. 2 shows representative dot plots of peripheral blood mononuclear cells (PBMCs) in urine show reduced staining quality after incubation with MOPS buffer and formaldehyde for 22 hours (+/−2 hours). Gating strategy for T Cells: lymphocyte scatter-gate. Selection of CD3+ T Cells. Discrimination CD4+ T Cells vs. CD8+ T Cells. Gating strategy for macrophages: monocyte scatter-gate. Selection of CD14+ CD36+ macrophages. (A) Fresh PBMCs, fully stained. (B) PBMCs incubated in urine with MOPS buffer and 1% formaldehyde for 22 hours (+/−2 hours)
Figure 3:
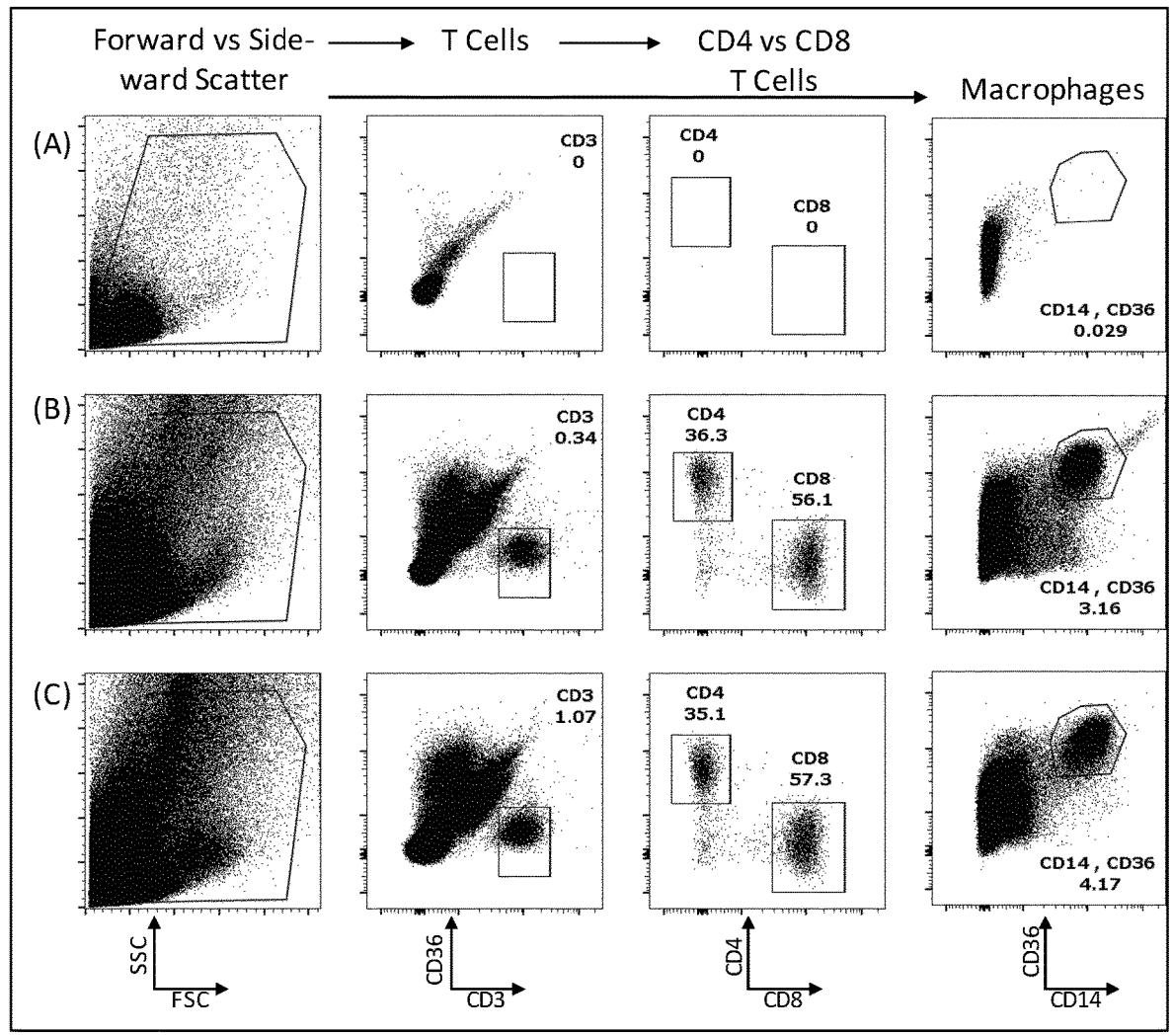
FIG. 3 shows representative dot plots of urinary leukocytes. Staining quality and percentages of populations of conserved sample after 22 hours and fresh sample are comparable. Gating strategy for T cells: exclusion of debris (low FSC and SSC) and large events (very high FSC and SSC). Selection of CD3+ T cells. Discrimination CD4+ T cells vs. CD8+ T Cells. Gating strategy for macrophages: exclusion of debris (low FSC and SSC) and large events (very high FSC and SSC). Selection of CD14+ CD36+ macrophages. (A) Fresh patient specimen (<6 hours after voiding), unstained. (B) Fresh patient specimen (<6 hours after voiding), stained. (C) Conserved patient specimen after 22 hours (+/−2 hours) at 4° C., stained.
Figure 4:
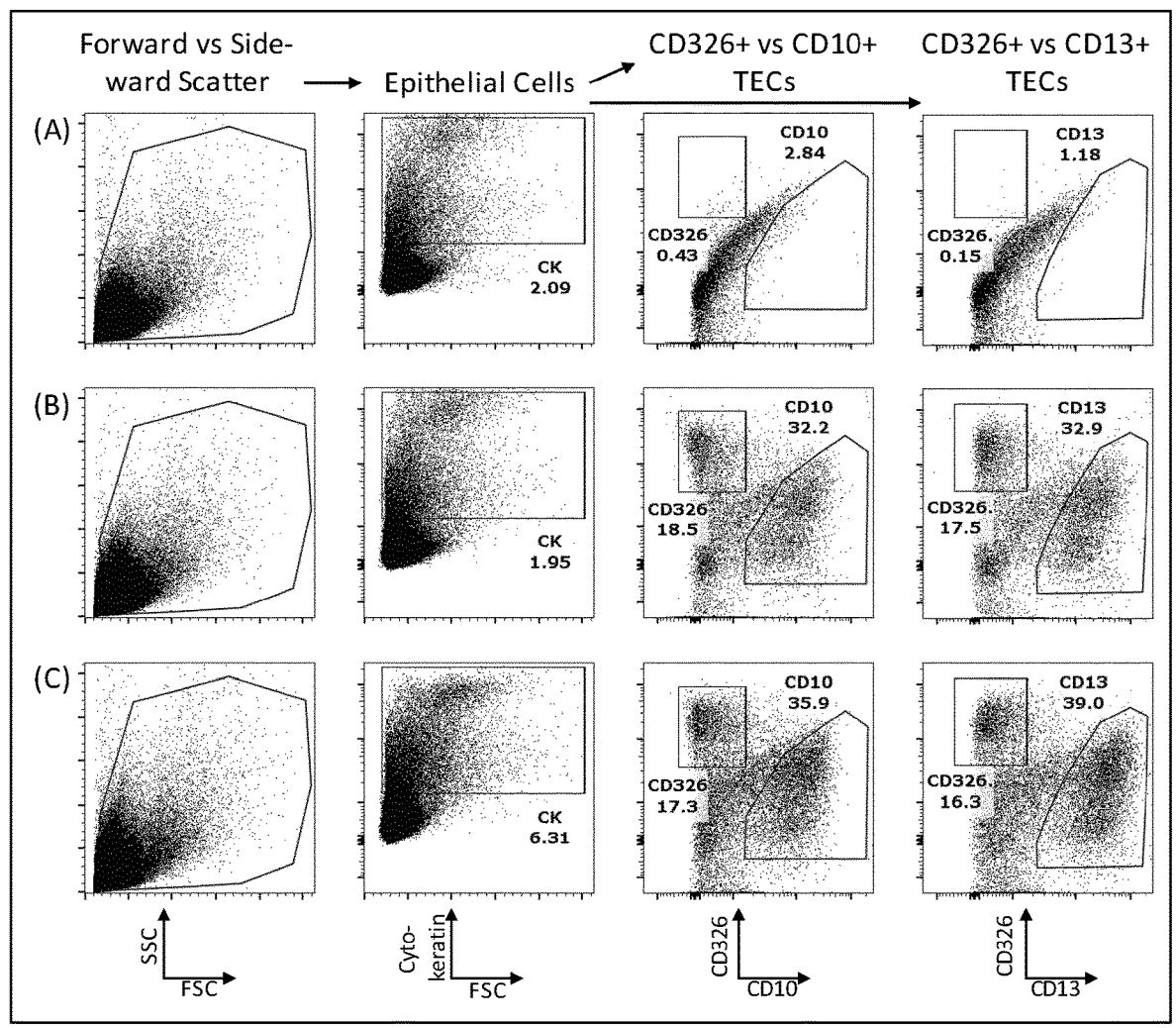
FIG. 4 shows representative dot plots of urinary epithelial cells. Staining quality and percentages of populations of conserved sample after 22 hours and fresh sample are comparable. Gating strategy for tubular epithelial cells (TECs): exclusion of debris (low FSC and SSC) and very large events (very high FSC and SSC). Selection of epithelial cells (cytokeratin+). Discrimination CD326+ (=EpCAM) TECs and CD10+ or CD13+ TECs. (A) Fresh patient specimen (<6 hours after voiding), fixated and permeabilized for intracellular staining, single stain for cytokeratin, isotype-control for CD326, CD10 and CD13. (B) Fresh patient specimen (<6 hours after voiding), fixated and permeabilized for intracellular staining, fully stained. (C) Conserved patient specimen after 22 hours (+/−2 hours) at 4° C., followed by permeabilization, fully stained.
Figure 5:
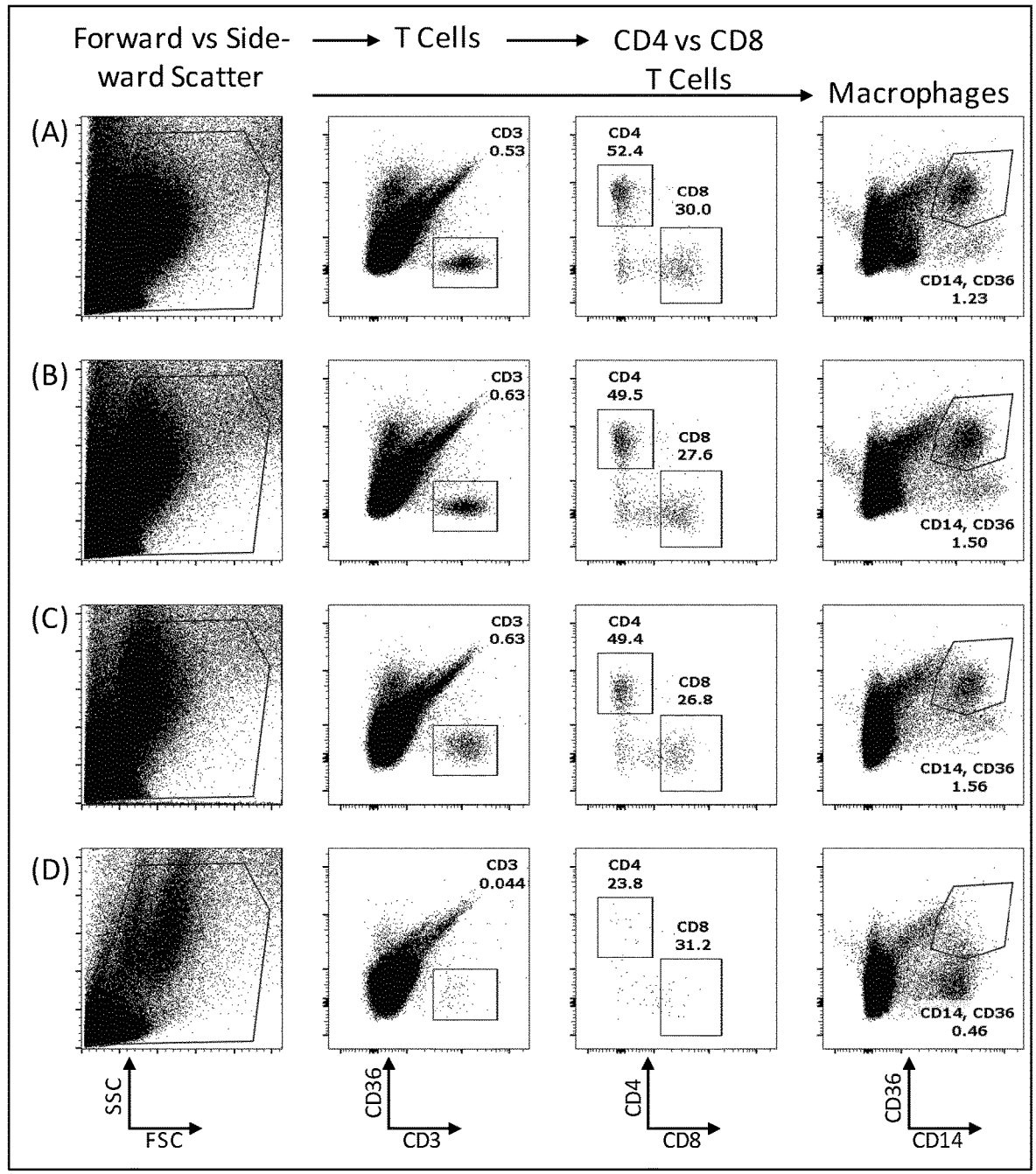
FIG. 5 shows the staining quality and percentages of populations of urinary leukocytes from conserved sample remain stable for up to 6 days, whereas leukocyte populations in non-fixated urine specimen disappear after 6 days (see FIG. 4D). Gating strategy for T cells: Exclusion of debris (low FSC and SSC) and large events (very high FSC and SSC). Selection of CD3+ T Cells. Discrimination CD4+ T Cells vs. CD8+ T cells. Gating strategy for macrophages: Exclusion of debris (low FSC and SSC) and large events (very high FSC and SSC). Selection of CD14+ CD36+ macrophages. Representative FACS plots shown. (A) Conserved patient specimen after 22 hours (+/−2 hours) at 4° C. (B) Conserved patient specimen after 3 days at 4° C. (C) Conserved patient specimen after 6 days at 4° C. (D) Patient specimen without conservation after 6 days at 4° C.
Figure 6:
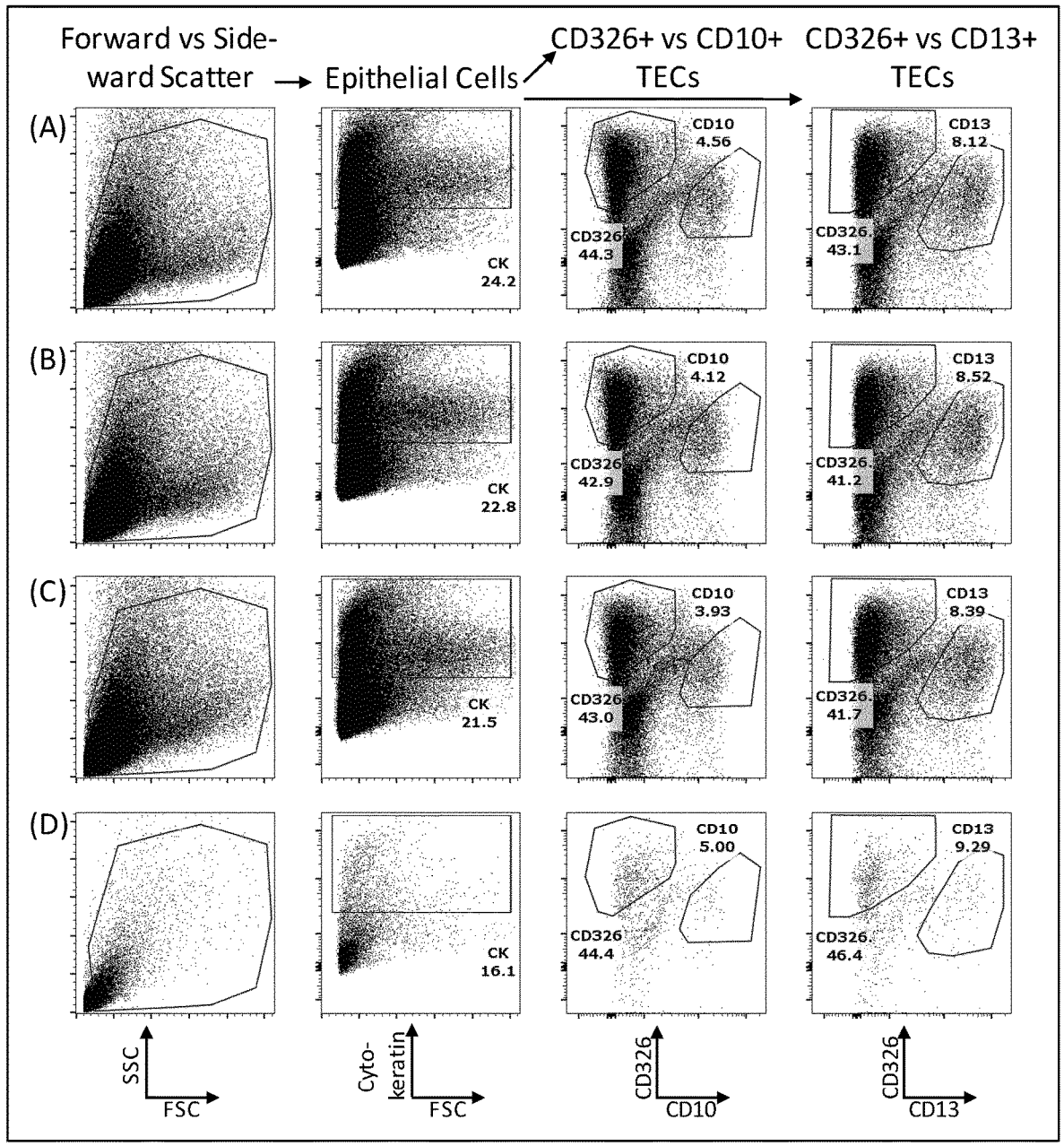
FIG. 6 shows the staining quality and percentages of populations of urinary epithelial cells from conserved sample remain stable for up to 6 days, whereas cell populations in non-fixated urine specimen almost disappear after 6 days (see FIG. 5 D). Gating strategy for tubular epithelial cells (TECs): Exclusion of debris (low FSC and SSC) and very large events (very high FSC and SSC). Selection of epithelial cells (cytokeratin+). Discrimination CD326+ (=EpCAM) TECs and CD10+ or CD13+ TECs. Representative FACS plots shown. (A) Conserved patient specimen after 22 hours (+/−2 hours) at 4° C. (B) Conserved patient specimen after 3 days at 4° C. (C) Conserved patient specimen after 6 days at 4° C. (D) Patient specimen without conservation after 6 days at 4° C.

However, incubation of the urine specimen with formaldehyde and MOPS buffer for at least 20 hours resulted in poor staining quality with diminished separation of positive and negative cells (FIG. 2) and thus a decrease in detectable cells.

In order to achieve a gentler fixation of cells, the inventors next introduced formaldehyde releasers such as, but not limited to, imidazolidinyl urea (IU) instead of direct addition of formaldehyde. The chemical group of formaldehyde releasers is used for example as a preservative in cosmetic products and is characterized by a slow release of formaldehyde-groups from a more complex molecule. When using this chemical agent, staining quality was only marginally impaired in comparison to fresh urine samples (FIGS. 3-6). Hence, the inventors were able to detect similar counts of urinary cells after 22 hours (+/−2 hours) compared to fresh samples (FIG. 7A). Furthermore, detected similar numbers of urinary cells were detected even after 3 and 6 days compared to samples analysed after 1 day (FIGS. 7B and 7C).

Liquid MOPS buffer and powdery imidazolidinyl urea are added in corresponding concentrations (see 2d) to the urine sample. By inverting the sample several times, the powder (IU) dissolves and all components are mixed sufficiently. Afterwards, the sample can be stored at 4° C. for 22 hours, 3 days, 6 days or potentially even longer for later sample preparation, i.e. antibody-based staining of cells, and flow cytometric analysis.

The method of the invention allows delayed sample preparation and analysis of human urinary cells through an easy conservation procedure. Both components (IU and MOPS buffer) are simply added to the urine specimen. After inverting the sample several times it can be stored in the fridge (4° C.) for 22 hours, 3 days, 6 days or potentially even longer. This enables centralized and standardized analysis facilitating multicentre studies as well as future diagnostic use in more peripheral clinics and outpatient care. Another important advantage of the method of the invention is increased safety when working with human samples, as cells will be dead after fixation. Furthermore, the conservation procedure leads to fixation of the cells, thus enabling to start directly with permeabilization for intracellular staining after a centrifugation step.

So far, the inventors have analyzed 15 samples for T Cell counts (which stain positive for CD3 and CD4 or CD3 and CD8) and Macrophages (positive for CD14 and CD36) and 9 samples for counts of kidney-derived tubular epithelial cells (positive for cytokeratin and CD326 (EpCAM) or cytokeratin and CD10 and CD13), respectively, after 22 hours (+/−2 hours). For time points after 3 days and 6 days, the inventors have acquired data from 10 samples for both T cells and tubular epithelial cells, respectively.

Every urine specimen was split equally allowing to compare cell counts of the conservation method of the invention after a certain time to a reference sample. Conserved samples stored for 22 hours (+/−2 hours) at 4° C. were referenced to a sample freshly prepared and analyzed directly upon receipt. Conserved samples stored for 3 days or 6 days at 4° C. were referred to samples conserved in the same way with the method of the invention and stored for 22 hours (+/−2 hours) at 4° C. before staining and analysis.

Specimen were acquired from patients with diverse renal pathologies, including: Acute Kidney Injury (AKI), Diabetic Nephropathy, Acute Rejection of a Kidney Transplant, Granulomatosis with Polyangiitis (GPA) with Renal Involvement, Systemic Lupus Erythematosus (SLE) with Renal Involvement, Rapid-progressive Glomerulonephritis (RPGN), IgA Nephropathy.

Figure 7:
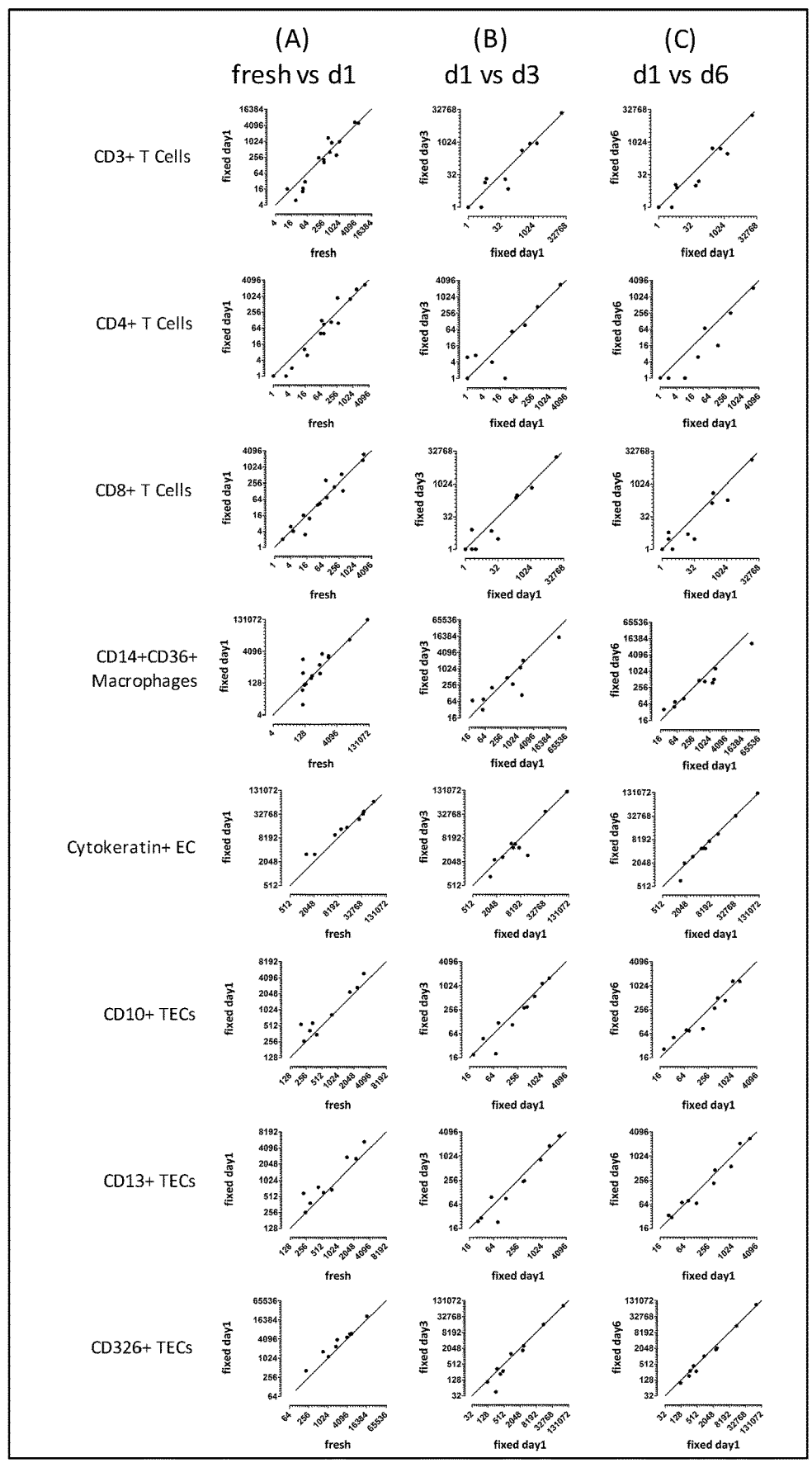
FIG. 7 shows the total cell counts of analyzed urinary leukocyte and epithelial cell populations remain stable for 22 hours, 3 days, 6 days or potentially even longer when conserved and stored at 4° C. Each dot represents the absolute cell number from each patient in both conditions (that is storage times). The diagonal line indicates identical cell amounts (slope=1) in both conditions, therefore dots on or close to this line represents measurements with equal or very similar cell numbers in both conditions. (Column A) Total cell counts from fresh patient urine specimens (<6 hours after voiding) and from equivalent volume of conserved patient urine specimens after 22 hours (+/−2 hours) at 4° C. (Column B) Total cell counts from conserved patient urine specimens after 22 hours (+/−2 hours) at 4° C. and from equivalent volume of conserved patient urine specimens after 3 days at 4° C. (Column C) Total cell counts from conserved patient urine specimens after 22 hours (+/−2 hours) at 4° C. and from equivalent volume of conserved patient urine specimens after 6 days at 4° C.

Comparison of total cell counts for samples from each time point and corresponding reference samples is presented in FIG. 7.

It is possible, that the hereby claimed method can be applied in diagnostics and monitoring of various renal diseases. So far, analysis of urinary cells was described for following entities:
Lupus nephritis
acute kidney injury
rejection after kidney transplantation
ANCA Vasculitis
diabetic nephropathy
IgA nephropathy
renal stones (nephrolithiasis)
bladder cancer Considering the variety of medical conditions, it is likely that the method according to the invention can be used for any renal or urologic disease or any disease that leads to altered cell composition in the urine.

Methods and Materials

Concentration imidazolidinyl urea: 20 mg/ml of total volume (Urine+MOPS)
Concentration MOPS buffer: 1 mol/l
Composition MOPS buffer (1 mol/l, for 100 ml):
20.95 g MOPS
0.82 g anhydrous sodium acetate (NaAc anhydrite)
1.85 g EDTA
Fill up to 100 ml with Aqua dest.
Adjust pH to 7 with NaOH
pH MOPS buffer: 7
Proportion of MOPS buffer of Total Volume: 1:3
Proportion of Urine of Total Volume: 2:3
60 ml urine, 30 ml buffer and 1800 mg imidazolidinyl urea (IU) were mixed. The final concentration of IU was 20 g/l.

Example 2: Establishment of a Sample Preservation System

Currently, a fresh urine sample is required for the flow cytometric analysis of urine cells (maximum 4-6 h after sample collection), which makes sample logistics difficult. The analysis of fresh samples requires an immediate transport of the sample, and the appropriately trained laboratory personnel and instrument capacities must be available for the analysis. At large clinics with maximum care, an essay based on fresh samples is feasible, but makes the analysis cost-intensive. It is almost impossible to use it in smaller hospitals or outpatient clinics. Currently, there is no established sample logistics for conserving urine cells for later flow cytometric analysis. Therefore, the inventors have developed a preservation method that preserves the cells in a special container for at least 6 days. The difficulty here was not only to preserve the cells, but also not to change the cells in such a way that no meaningful staining for flow cytometry is possible after preservation. In addition, the preservation system must be as simple and uncomplicated as possible in order to be accepted by the users (medical personnel in routine operation). By combining a buffer substance and a formaldehyde releasing compound in a two-step process, the inventors succeeded in preserving the cells for at least six days. All that is required is to add a urine sample to a container containing a buffer and then add a formaldehyde releasing compound (in powder or tablet form). Alternatively, the container is equipped with the buffer compound and formaldehyde releasing compound in a way that enables stable shelf life for both, and the urine sample is added, optionally after addition of water, upon opening of the container from its packaging.

Figure 8A:
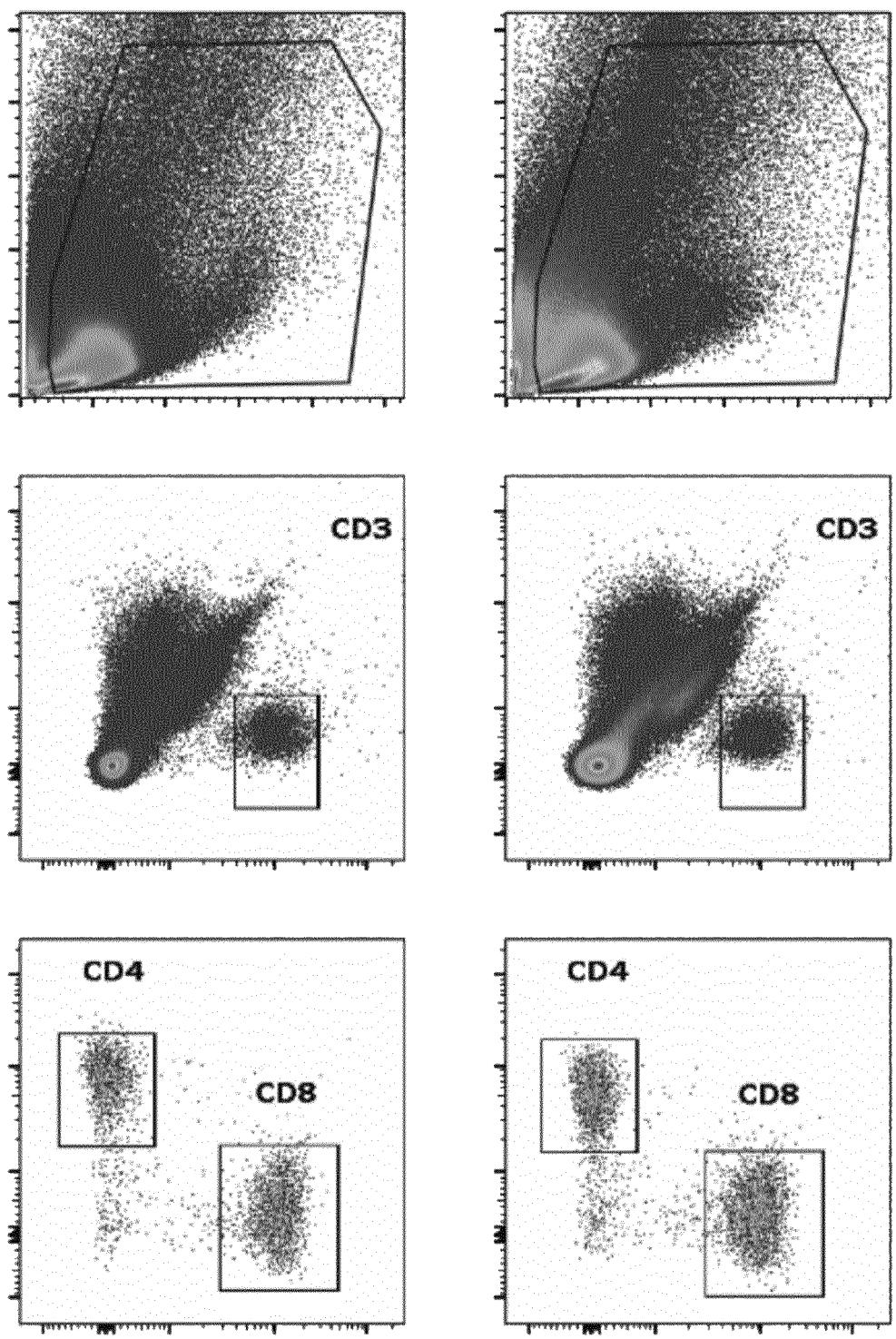
FIG. 8 shows the preservation of cells in urine. A. Representative flow cytometry plots of staining on fresh cells and after 20 h preservation. No qualitative deterioration of staining is observed. B. Comparison of cell numbers in urine in the freshly measured sample and after 24 h preservation, each point represents one sample. The gray line shows absolutely identical cell numbers, the dashed line shows the regression analysis of the actually measured values. There is a high degree of agreement, i.e. an almost constant cell count despite preservation.
Figure 8B:
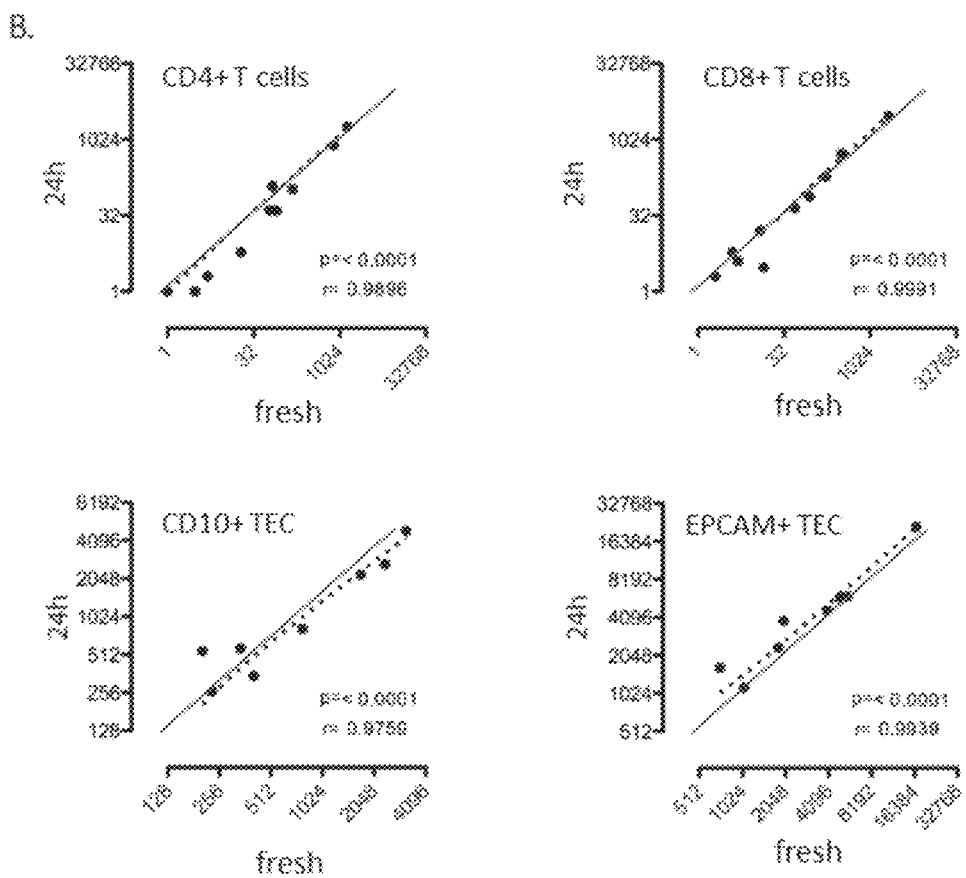

The sample can then be stored and/or transported. With this preservation, staining and flow cytometry of the cells can be performed without compromising the quality of the analysis. A comparison of the analysis of fresh urine and after one, three or six days of preservation showed almost identical cell counts and a linear correlation of the measured cell counts (Pearson correlation for $CD3^+CD4^+$, $CD3^+CD8^+$ and proximal and distal TEC, p<0.001 for all, r=0.9530–0.9998, median r 0.9982, FIG. 8).

The system is user-friendly and does not require a complicated or time-consuming protocol. It is easy to implement within 30 seconds, which is the prerequisite for practical implementation.

Example 3: Comparison with Published Protocols of Cell Preservation

WO 2014/029791 A1 shows a flow cytometric analysis of cells that have been treated with different variants of a fixation protocol. The following reagents were used to preserve the cells and each solution was A to E was diluted 1:50 with the cell sample:
  A. 25% w/v diazolidinyl urea
  B. 1.5% w/v aurintricarboxylic acid
  C. 0.8% w/v sodium fluoride
  D. 10% w/v EDTA
  E. 4.5% w/v glyceraldehyde The mentioned variants for cell preservation were compared with the protocol according to the invention, i.e. the solutions A to E were each diluted 1:50 with urine. Aurintricarboxylic acid rapidly precipitates when added to urine, rendering it unusable for the purpose of the protocol of the present invention. Also EDTA alone (0.2% final concentration) precipitates in urine.

The three other ingredients (glyceraldehyde, diazolidinyl urea and sodium fluoride) were tried at the concentration given in WO 2014/029791 A1 for the preservation of urine cells in three patient urine samples and compared with the protocol. For all three substances, the quality of the staining in the flow cytometric analysis deteriorated significantly.

Example 4: Kinetics of Fixation of Immune Cells Using IU

IU fixation was performed with different incubation times: 5 min, 30 min, 1 h, 5 h, 1 day. Subsequentyl, permeabilization was performed using Perm/wash (unfixed cells would have to break). Measurement and cell counting was performed at MACSquant followed by evaluation via SSC/FSC and ZZ.

Controls: positive: PFA-fixed cells; negative: unfixed cells.

After 5 h of incubation in all replicated 100% of cells were fixed. The protocol according to the invention even yielded higher amounts of recovered cells in comparison to the commercial kit, therefore values>100% were observed.

Example 5: T cells as Biomarkers for Lupus Nephritis

Lupus nephritis (LN) is one of the most common and serious complications of systemic lupus erythematosus (SLE). Under standard therapy with cyclophosphamide or mycophenolate mofetil (MMF) there is a risk of serious side effects, such as severe infections under immunosuppression. On the other hand, as repeatedly shown in studies, only about 45% of patients achieve complete remission under therapy, which implies significant morbidity. In addition, uncontrolled disease activity as well as side effects of the therapy repeatedly lead to deaths. Biomarkers could effectively help to improve the prognosis of LN by early diagnosis and individualized therapy based on better prognosis assessment and therapy control.

Figure 9:
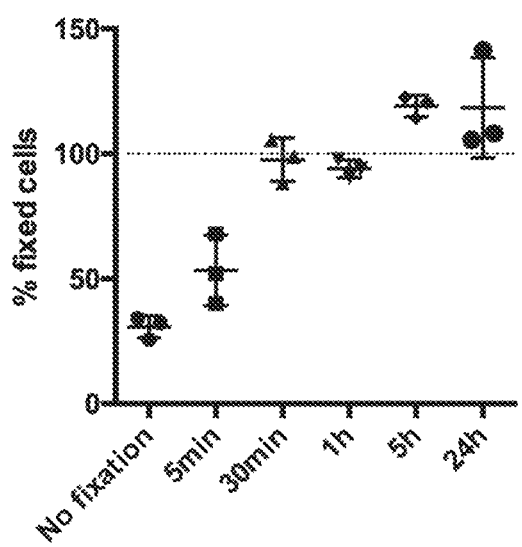
FIG. 9 shows the kinetics of the fixation of immune cells using IU. Displayed is the percentage of fixed cells in comparison to cells fixed using a commercial cell fixation kit. The cells were incubated with IU for 5 min, 30 min, 1 h, 5 h and 24 h. Experiments were performed in replicates.

In a cohort of 147 SLE patients and 186 urine samples, the inventors were able to demonstrate that the amount of $CD4^+$ T cells in the urine identified patients with active lupus nephritis with high sensitivity (100%) and specificity (98%) (FIG. 9. area below the ROC curve, AUC 0.99). SLE patients without kidney involvement showed hardly any T-cells in the urine even with increased disease activity, and SLE patients with known kidney involvement but without increased disease activity showed only few T-cells in the urine. In contrast, all patients with proliferative lupus nephritis (the most common form of LN) had increased levels of T cells in their urine. Interestingly, in the few patients with active, non-proliferative LN (such as LN class I or V), hardly any T cells were observed, which could be used to differentiate the individual LN subclasses. In the investigated cohort of 147 SLE patients, the determination of T-cells in urine was clearly superior to routine markers such as creatinine, proteinuria and urine sediment.

Even more interesting for clinical use is the fact that the amount of T cells in urine in the course of therapy allows a correlation to the response to treatment at an early stage. An early adaptation of the therapy in the sense of a personalized treatment would be conceivable with the aid of biomarkers.

In a small cohort of SLE patients, the inventors were also able to show that the amount of memory/effector T cells (EM T cells) in urine at the time of diagnosis can predict therapy response 6 months later. All patients with a higher frequency of EM T cells showed no response after induction therapy.

In summary, lupus nephritis can be i) diagnosed with T-cells in urine, ii) the response to treatment monitored and iii) the prognosis estimated.

Example 6: Combination of T Cells and Tubule Epithelial Cells for Diagnosis of Kidney Transplant Rejection Kidney transplantation is probably the best therapy for terminal renal failure. However, acute rejection of the transplant is a constant concern, requiring permanent immunosuppressive use and regular monitoring of graft function. At present, there are no reliable non-invasive markers for acute rejection of the transplant, which is why a kidney biopsy with corresponding risks must be performed if suspected.

Figure 10:
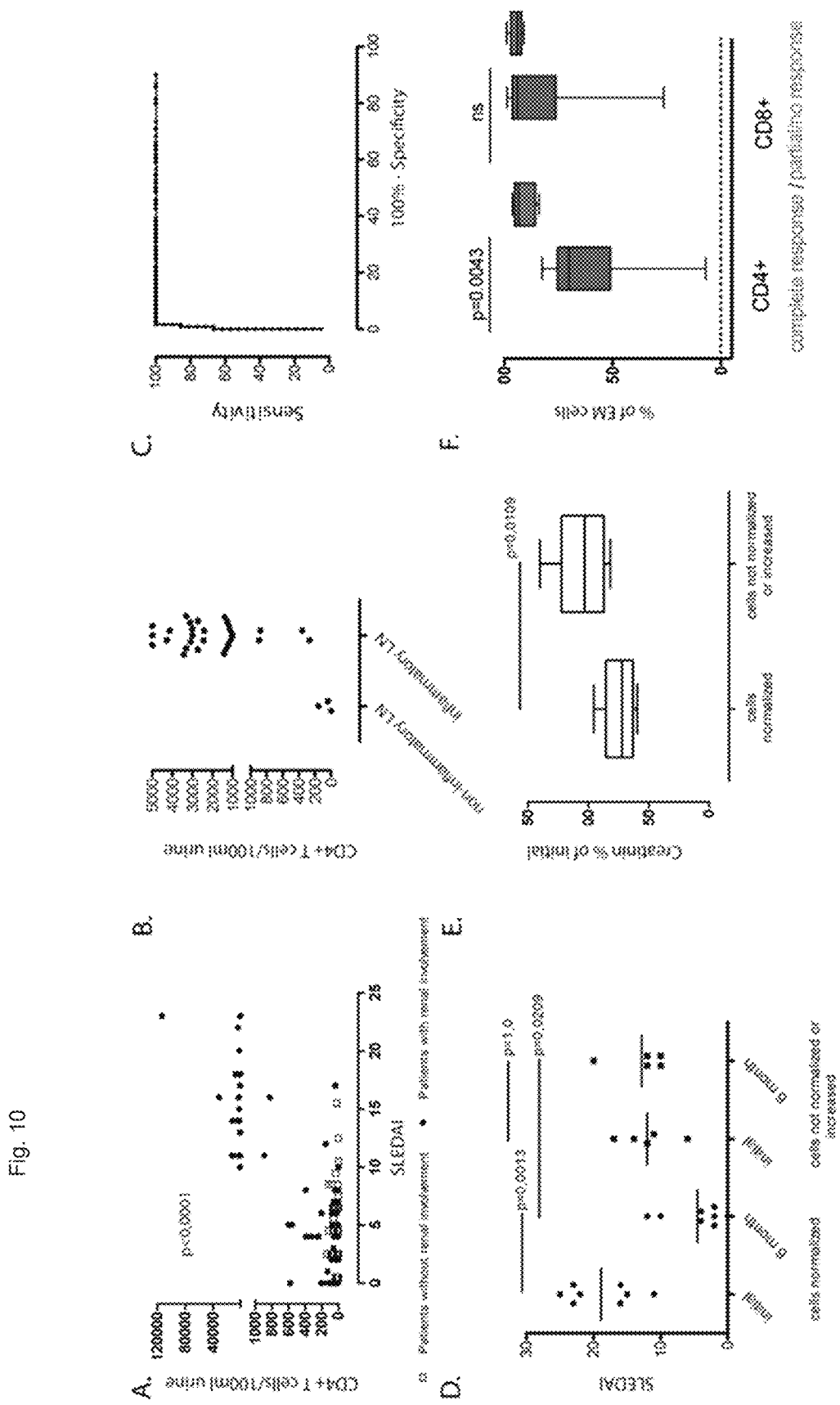
FIG. 10 shows $CD4^+$ T cells as biomarkers for active lupus nephritis (LN). A. Correlation of $CD4^+$ T cell count per 100 ml urine with disease activity (measured as SLE-DAI). Each open square represents one SLE patient without renal involvement, filled circles represent one SLE patient with known renal involvement. B. Comparison of the amount of $CD4^+$ T cells in the urine with a simultaneous kidney biopsy. All patients with inflammatory LN (proliferative LN) show increased levels of T cells in urine. C. ROC curve for the detection of proliferative/inflammatory LN in SLE patients using the amount of $CD4^+$ T cells in urine (sensitivity of 100% and specificity of 98.0%). D. Patients who normalize their $CD4^+$ T cell counts under therapy show a significant reduction of their disease activity, patients with persistent or increasing $CD4^+$ T cell counts in urine show no reduction of their disease activity. E. Patients with normalized $CD4^+$ T cells in urine have a better creatinine increment after six months of therapy than patients with persistence of T cells in urine. F. The effector/memory (EM) $CD4^+$ T cell count predicts response to therapy after 6 months of induction therapy.
Figure 11:
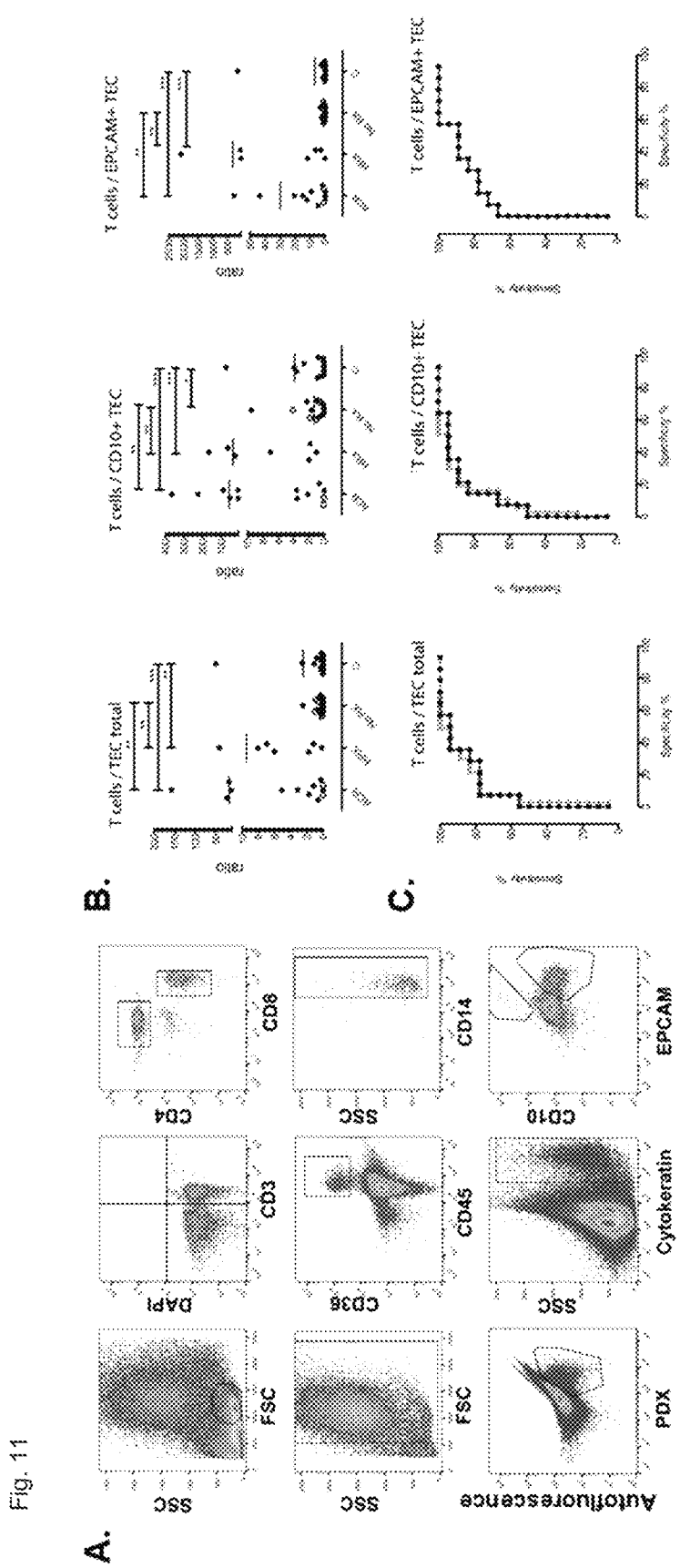
FIG. 11 shows different cell populations in urine as markers for acute kidney transplant rejection. A. Representative flow cytometry plots for the detection of T-cells (CD3, CD4, CD8), macrophages (CD45, CD36, CD14), podocalyxin-positive cells (PDX, as surrogate for podocytes) and renal tubule epithelial cells (TEC; cytokeratin, CD10, EPCAM) B. Amount of T cells in relation to TEC and $PDX^+$ cells in patients with acute cellular rejection (ACR), humoral rejection (HRX), patients with graft degeneration without rejection (No Rx) and patients with stable graft function (Contr.). C. ROC curves show a good diagnostic significance of the combination of T cells and TECs or $PDX^+$ cells in urine (AUC 0.9). Black line: comparison of patients with rejection with the No RX group; grey line: data including contrast patients with stable graft function. SSC=sideways scatter; FSC=forwards scatter; DAPI=dead cell dye.

In a cohort of 63 kidney transplant patients, the amount of different immune cells (CD4+ and CD8+ T cells, monocytes/macrophages) as well as renal tubule epithelial cells (proximal and distal TECs) and podocytes ($PDX^+$ cells) was investigated. A kidney biopsy was performed in 39 of the examined patients due to a deterioration of NTX function and the results were directly compared with the biopsy result as gold standard. In addition, 24 patients with stable NTX function were examined as control groups. By combining the amount of T cells (total amount of T cells or $CD4^+$ or $CD8^+$ T cells) and TEC in the urine as T cell/TEC ratio, a good separation of patients with and without rejection was achieved (FIG. 10, area below the ROC curve 0.90). In a cohort of 64 kidney transplant patients in a clinically very relevant scenario, a combination of T cells and tubule epithelial cells in the urine showed good sensitivity and specificity (FIG. 10, area below the ROC curve 0.90).

Example 7: Further Data in Other Diseases

In patients with acute renal failure (ANV), it was shown that the amount of TECs in the urine correlated with the extent of renal damage (measured as ANV stage). In addition, stem cell-like cells could be detected in urine in patients with ANV, which only occurred in patients recovering from ANV (possible regeneration markers).

In patients with glomerulonephritis associated with ANCA, similar to LN, it was demonstrated that the amount of T-cells in the urine is a biomarker for active renal inflammation.

The invention claimed is:

1. A method for analysing urinary cells, the method comprising the steps of:
   contacting a urine sample obtained from a patient with
   a. a buffer substance suitable to create and/or maintain a pH value in the range of 6 to 8, within said urine sample, and
   b. a formaldehyde releasing compound
   yielding a preserved urine sample,
   storing the preserved sample prior to analysing the urinary cells at a temperature of −80° C. to 10° C.;
   analysing urinary cells within said preserved urine sample.

2. The method according to claim 1, wherein said urine sample is contacted with said buffer substance and said formaldehyde releasing compound not later than 6 h, 5h, 4 h, 3h, 2h or 1h after sampling.

3. The method according to claim 1, wherein said formaldehyde releasing compound is selected from imidazolium urea, hexamethylenetetramine chloroallyl chloride, diazolidinyl urea, 1,3-bis(hydroxymethyl)-5,5-dimethylimidazolidine-2,4-dione, 1-(hydroxymethyl)-5,5-dimethyl-2,4-imidazolidindione or hexamethylenetetramine.

4. The method according to claim 1, wherein said buffer substance is selected from 3-(N-morpholino) propanesulfonic acid, phosphate buffered saline sodium hydrogencarbonate, tris (hydroxymethyl) aminomethane and 4-(2-hydroxyethyl)-1-piperazineethanesulfonic acid.

5. The method according to claim 1, wherein the buffer substance is provided in a buffer solution.

6. The method according to claim 1, wherein the urine sample is contacted first with the buffer substance and then with the formaldehyde releasing compound.

7. The method according to claim 1, wherein the final concentration of the buffer substance is between 5% (w/v) and 10% (w/v) and/or the final concentration of the formaldehyde releasing compound is between 0.5% (w/v) and 5% (w/v).

8. The method according to claim 1, wherein said analysing comprises a cytometric analysis of said urinary cells with said preserved urine sample.

9. The method according to claim 8, wherein said cytometric analysis comprises a flowcytometric analysis.

10. A method for diagnosing a medical condition, the method comprising analysing urine cells within a urine sample obtained from a patient with a method according to claim 1.

11. The method according to claim 10, wherein said medical condition is selected from Lupus nephritis, acute kidney injury, rejection after kidney transplantation, ANCA vasculitis, diabetic nephropathy, IgA nephropathy, nephrolithiasis, and bladder cancer.

* * * * *